(12) United States Patent
Murphy

(10) Patent No.: US 6,235,051 B1
(45) Date of Patent: May 22, 2001

(54) METHOD OF STENT-GRAFT SYSTEM DELIVERY

(76) Inventor: Timothy P. Murphy, 107 Pratt St., Providence, RI (US) 02906

( * ) Notice: Subject to any disclaimer, the term of this patent is extended or adjusted under 35 U.S.C. 154(b) by 0 days.

(21) Appl. No.: 09/121,290

(22) Filed: Jul. 22, 1998

Related U.S. Application Data

(60) Provisional application No. 60/069,771, filed on Dec. 16, 1997.

(51) Int. Cl.[7] .......................................... A61F 2/06
(52) U.S. Cl. .......................................... 623/1.12; 623/1.11
(58) Field of Search ............................... 623/1, 12, 1.12, 623/1.11, 1.13, 1.2, 1.23, 1.34, 1.35

(56) References Cited

U.S. PATENT DOCUMENTS

| 5,246,452 | * | 9/1993 | Sinnott | 623/12 X |
| 5,549,635 | * | 8/1996 | Solar | 623/1 X |
| 5,591,226 | * | 1/1997 | Trerotola et al. | 623/1 |
| 5,667,523 | * | 9/1997 | Bynon et al. | 623/12 X |
| 5,713,948 | * | 2/1998 | Uflacker | 623/12 X |
| 5,776,186 | * | 7/1998 | Uflacker | 623/12 X |
| 5,830,217 | * | 11/1998 | Ryan | 606/108 |

* cited by examiner

Primary Examiner—Jeffrey A. Smith
(74) Attorney, Agent, or Firm—David J. Powsner; Nutter, McClennen & Fish LLP

(57) ABSTRACT

A vascular stent-graft system comprises a stent-graft with an expandable tip and a restraining member disposed about at least a portion of that tip. The restraining member constrains expansion of the tip, even absent contact with a delivery device by which the stent-graft is deployed. Thus, unlike prior art designs, the tip can be partially positioned and at least temporarily freed from the grasp of a deployment device without risk that the tip will be prematurely expand into a potentially undesirable fit in the aorta.

15 Claims, 2 Drawing Sheets

METHOD OF STENT-GRAFT SYSTEM DELIVERY

BACKGROUND OF THE INVENTION

This application claims the benefit of priority of U.S. patent application Ser. No. 60/069,771, filed Dec. 16, 1997.

This invention pertains to medical devices and procedures and, more particularly, to improved stent grafts and methods of deployment thereof. The invention has application in the repair of vasculature, such as aneurysms of the abdominal aorta.

Aneurysms of the abdominal aorta, defined as enlargement to greater than 1.5 times the normal diameter, occur in 36 per 100,000 individuals annually, with an overall prevalence of 6% of men by the age of 80, and 4.5% of women by the age of 90. Rupture of an abdominal aortic aneurysm is associated with up to a 62% death rate prior to reaching a hospital, and with a death rate over 50% for those who reach the hospital for emergency surgery. Aneurysm rupture is related to size; the 5-year incidence of rupture of 4 to 5 cm abdominal aortic aneurysms range from 3 to 12 percent, whereas the 5-year risk of rupture of aneurysms greater than 5 cm diameter ranges from 25% to 41%. Two series of patients with abdominal aortic aneurysms followed without treatment in the 1950's demonstrated 5-year survival of 4% and 19%. Subsequent series have demonstrated 5-year survival of 49% to 84% in patients who undergo elective surgery for abdominal aortic aneurysm.

Surgical treatment of abdominal aortic aneurysms has been the standard therapy since its introduction in 1951. Replacement of an aneurysm with a prosthetic graft is the current standard therapy, but elective surgery is associated with a 5% death rate in low-risk patients, 20% major complication rate, lengthy hospitalization, and significant cost. Additionally, many patients have comorbid conditions that preclude elective surgery, such as heart disease or chronic lung disease.

In 1991, Dr. Juan Parodi described a method of aneurysm repair that involved placement of an intraluminal aortic graft through an excision in the femoral artery, averting the risk and expense of major abdominal surgery through a midline or flank incision. The method involved surgical exposure of the common femoral artery in the upper thigh, and placement of an 22 French (8 mm outer diameter) introducer through the femoral artery, iliac artery, and into the aorta. Through this introducer, a prosthetic tube graft attached at both ends to a self-expanding intravascular stent were passed into the aorta. After positioning using fluoroscopic x-ray guidance, the introducer is retracted, and the stents dilated using balloon angioplasty. The stents served to anchor the graft in the aorta.

Although successful at excluding aneurysms limited to the abdominal aorta, the majority (80%) of aneurysmal abdominal aortas are dilated to the termination of the aorta, or extend into one or both iliac arteries. For such patients, placement of a simple "tube" graft in the aorta is not sufficient to prevent subsequent aneurysm expansion or rupture.

Patients with aortic aneurysms that extend to the aortic termination or into the iliac arteries require placement of a "bifurcated" graft, or an aortic Y-graft. The placement of a bifurcated stent-graft into the aorta through a common femoral arteriotomy poses many technical challenges. First, introducer sheaths must be sizable, ranging from 24 to 30 French (inner diameter, or 9 to 11 mm diameter outer diameter). Placement of the contralateral iliac limb requires snaring or retrieval of the limb via a catheter placed in the contralateral femoral artery, or reassemble of a bifurcated graft in the body from components. Usually, components include an aortic limb and a single iliac limb placed through one femoral artery, and a second iliac limb placed through the other femoral artery in the opposite leg. This system requires engagement of an opening in the aortic segment with the iliac segment after introduction and deployment of the aortic segment in the aorta.

Disadvantages of these methods include being cumbersome, and the potential for leakage of blood into the aneurysm sac through the junction of the components due to inadequate seal after placement or due to subsequent disjunction. They have the disadvantage of requiring surgical access of one or both femoral arteries for placement. Additionally, many patients do not have iliac arteries of sufficient size to allow placement of large introducer sheaths through them into the aorta. This may prevent the performance of the procedure, or may result in complications in the iliac arteries such as dissection, rupture, or transection.

In view of the foregoing, an object of this invention is to provide improved stent-grafts and methods of deployment thereof. A more particular object is to provide improved stent-grafts and methods for use in repair of vascular cavities, such as aneurysms of the abdominal aorta.

A related object of the invention is to provide improved such stent-grafts and methods as permit the repair of aneurysmal abdominal aortas that are dilated to the termination of the aorta or that extend into the iliac arteries.

A further related object of the invention is to provide improved such stent-grafts and methods as overcome the complications associated with the deployment of conventional stent-grafts.

Still another object of the invention is to provide stent-grafts that can be fabricated from existing materials and without the use of complicated manufacturing technologies and, hence, that can be produced at low cost and with high quality.

Yet still another object of the invention is to provide stent-grafts that can be emplaced without complicated and time-consuming surgical techniques.

SUMMARY OF THE INVENTION

The aforementioned objects are among those achieved by the invention, one aspect of which provides a vascular stent-graft system, comprising a stent-graft with an expandable tip and a restraining member disposed about at least a portion of that tip. The restraining member constrains expansion of the tip, even absent contact with a delivery device by which the stent-graft is deployed. Unlike prior art designs, the tip can be partially positioned and at least temporarily freed from the grasp of a deployment device without risk that the tip will be prematurely expand into a potentially undesirable fit in the aorta.

The stent-graft can be of any desirable configuration having at least one expandable tip. Typical configurations are tubular (with two such tips) or Y-shaped (with three such tips), each for placement at a respective end of the vascular region to be repaired. Though the tips are typically not tapered when in their expanded states, the distal ends of the restraining member can be. This facilitates moving the member and the tip it encases within the vasculature or removing the restraining member from the vasculature after deployment.

According to further aspects of the invention, the restraining member is a sleeve of fabric or web. In other aspects, the restraining member comprises a wrap, e.g., of suture or other thread-like material. In either event, the member preferably comprises a biocompatible material such as polyethylene, polytetraflouroethylene, polypropylene, nylon, or silk.

The restraining member, according to further aspects of the invention, can be detachably affixed, e.g., by way of a suture loop, a hook, an aperture, a button, a hook-and-loop, or interference or friction fit. This degree of affixation can be great enough to permit the tip or stent-graft to be positioned by grasping and pulling of the member, but not so great as to prevent the restraining member from being deliberately pulled off the tip, e.g., via a deliberate tug.

A related aspect of the invention provides a stent-graft system as described above where the restraining member is removed from the tip via motion in a central-to-peripheral direction, that is, motion in a direction away from a central portion of the stent graft and towards a peripheral portion of the tip. A sleeve-like restraining member that is slidably removable, for example, can be slid away from the central portion (or body) of the stent-graft and pulled off the tip. In the case of a thread-like restraining member that is wrapped around the tip (e.g., a suture wrap), a free end of the thread-like member can be pulled in the central-to-peripheral direction in order to unwind the wrap and, thereby, free the expandable tip. Removal via a central-to-peripheral motion is advantageous insofar as it minimizes the cavity volume required for deployment and insofar as it permits percutaneous deployment directly through the wall of the cavity or aneurysm.

According to further aspects of the invention, the restraining member can have a tab, a thread-like free end, a protrusion, or other such member by which it can be snared. This facilitates positioning the tip and, preferably, removing the restraining member therefrom. A radio-opaque portion can be provided on that tab, free end, protrusion, or other snareable member to facilitate locating it, the restraining member and/or the tip itself.

Further aspects of the invention provide methods for vascular treatment via the steps of (i) placing a stent-graft system of the type described above into a vascular cavity to be repaired, (ii) positioning the tips of the stent-graft into respective portions of that cavity, and (iii) removing the restraining members from the tips. Thus, for example, the method provides for repair of an aortic aneurysm by inserting the stent-graft system directly through the distended wall of the aneurysm and positioning the restraining member-sheathed tips in respective arteries disposed about the aneurysm. After each tip is positioned (or, alternatively, after one of more of them have been positioned) the restraining member covering that tip is removed, thus, allowing the tip to expand into fluid communication with the respective artery.

An advantage of the use of such a stent-graft system is that placement can be performed by surgically inserting the stent-graft directly into the aneurysm itself. Because the restraining member constrains expansion of its own (e.g., without contact with a delivery device by which the stent-graft is deployed) and because the restraining members are removed via central-to-proximal motion, the respective tips of the stent graft can be partially positioned and at least temporarily freed from the grasp of a deployment device without risk that the tip will be prematurely expand into a potentially undesirable fit in the cavity. A further advantage is that systems according to the invention can be inserted and deployed within the lumen of the artery (or other vascular cavity) via catheter or other "closed" surgical procedure.

These and other aspects of the invention are evident in the drawings and in the description that follows.

BRIEF DESCRIPTION OF THE DRAWINGS

A more complete understanding of the invention may be attained by reference to the drawings, in which.

DETAILED DESCRIPTION OF THE ILLUSTRATED EMBODIMENT

Figure 1:
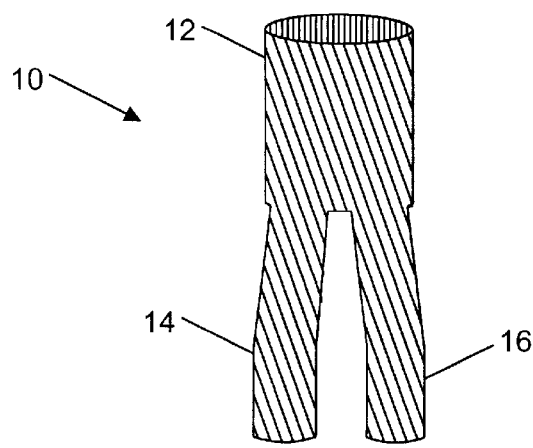
FIG. 1 depicts a bifurcated stent-graft of the type used in a stent-graft system according to the invention.

FIG. 1 shows a conventional bifurcated stent-graft 10 of the type used to practice the invention. The stent-graft comprises aortic limb or tip 12 and iliac limbs or tips 14, 16, each of which is intended for insertion into a respective one of the aortic artery, left iliac artery and right iliac artery to provide fluid flow therebetween.

The stent-graft 10, in general, and the tips 12, 14, 16, in particular, are of the self-expanding variety. Absent constraint, these members expand toward their fully-opened states, as shown in the drawing. Self-expanding stent-grafts of this variety are typically fabricated from metallic or synthetic wire hoops or braids encased in natural or mamnade fiber webs, such as polyethylene, polytetraflouroethylene, polypropylene, polyester, nylon, or silk. Polytetraflouroethylene (PTFE) or other coatings may be provided on the stent-grafts to ease insertion and to reduce coagulation or other buildups. Preferred bifurcated stent-grafts for use in practice of the invention are currently being used in FDA-approved clinical trials by Endovascular Technologies (EVT), Los Angeles, Calif.; Boston Scientific, Natick, Mass.; W.L. Gore, Co., Flagstaff, Ariz.; and Cook, Inc., Bloomington, Ind.

Though not shown illustrated herein, the invention may be practiced with bifurcated stent-grafts sized or intended for insertion in vascular cavities other than the abdominal aorta. The invention may also be practiced with stent-grafts of other configurations, e.g., tubal stent-grafts that have only two tips.

Figure 2:
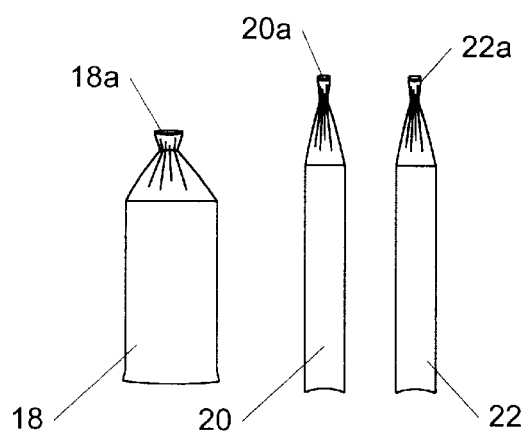
FIG. 2 depicts restraining members of the type used in a stent-graft system according to the invention.

FIG. 2 illustrates sheath-type restraining members 18, 20, 22 for use with a stent-graft system according to the invention. The members 18, 20, 22 encase tips 12, 14, 16, respectively, of stent-graft 10 in order to maintain them in at least partially compressed states. Along with the tabs 18a, 20a, 22a formed into the ends of members 18, 20, 22 and the tapered ends of those members, the members 18, 20, 22 facilitate deployment of the stent-graft 10 and, particularly, of the tips 12, 14, 16 in the respective vascular cavities.

Illustrated restraining members 18, 20, 22, otherwise known as capsules, are generally tubular in shape have protrusions or other constructions thereon that facilitate grasping. In the illustrated embodiment, these comprise tabs 18a, 20a, 22a formed at the distal ends of the capsules 18, 20, 22, as illustrated. As further shown in the drawings, the restraining members also have tapered portions at their distal ends. These facilitate pulling (or pushing) the restraining members through catheters or vasculature prior to, during and after deployment.

Figure 3:
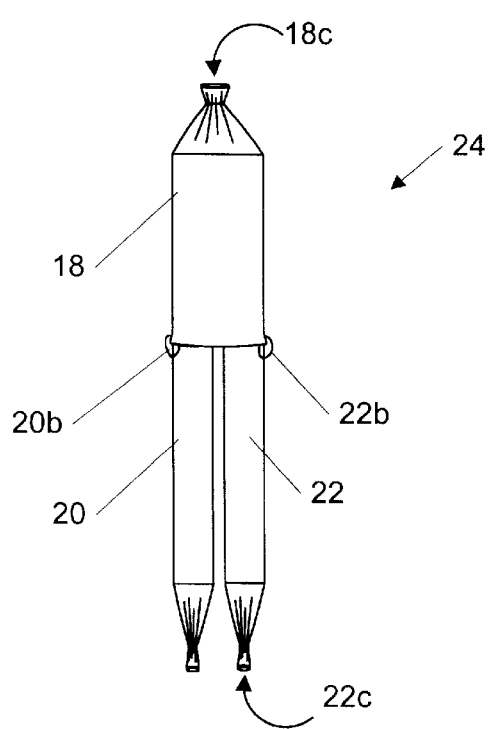
FIG. 3 depicts deployment of a stent-graft system according to the invention.

FIG. 3 illustrates a stent-graft system 24 according to the invention, in which the compressed limbs 12, 14, 16 of the stent graft 10 are encased in capsules 18, 20, 22. According to one practice of the invention, the stent-graft 10 is fabricated independently of the capsules 18, 20, 22. The system 24 is then formed by loading the limbs 12, 14, 16 of the stent-graft into the respective capsules 18, 20, 22. Other practices of the invention provide for concurrent fabrication of the stent-graft and capsules.

In a preferred practice, the capsule 18 corresponding to the aortic limb 12 of the stent-graft 10 has an aperture at its distal end 18c (i.e., the cephalad end) to facilitate passage of a guidewire. At least one of the iliac capsules 20, 22 likewise has an aperture, e.g., 22c, at its distal (or caudal) end. In one practice, the iliac capsules 20, 22 are detachably fastened to the aortic capsule 18 via friction or interference fit. Preferably, such attachment is via fine (5-0 or smaller) "break-away" absorbable cat-gut sutures loops 20b, 20c, as illustrated, or with other detachable structures such as a hooks, apertures, buttons, hook-and-loop arrangements.

The capsules 18, 20, 22 are comprised of any biocompatible materials that can be fabricated into shapes suitable for restraining the tips 12, 14, 16 in compressed states prior to and during deployment and for removal from the tips thereafter. Suitable materials include, for example, natural or manmade fiber webs, such as polyethylene, polytetraflouroethylene, polypropylene, polyester, nylon, or silk. They may also be coated with PTFE or other such agents to ease their deployment through an endoscope or catheter and into the vascular cavities. The capsules 18, 20, 22 preferably comprise a radio-opaque coating or material at least on tabs 18a, 20a, 22a to facilitate locating them by fluoroscopy during deployment.

In a preferred practice, the capsule material will be as thin as possible without compromising the integrity of the material and constraint of the undeployed stent-graft. Moreover, the capsules 18, 20, 22 will have diameters that are as small as possible, without making it unduly difficult to load the collapsed tips 12, 14, 16 therein. This particular constraint may not come into play, of course, in those embodiments wherein the tips are fabricated in concert with their respective capsules. Though the capsules 18, 20, 22 are preferably somewhat longer than the limbs 12, 14, 16 that they cover, they may also be shorter—though they preferably cover at least the distal ends of the tips 12, 14, 16.

Of course, the restraining members need not be fabricated from webs. Instead, for example, they may be fashioned by wrapping the respective tips 12, 14, 16 in compressed states with suture- or thread-like materials. Alternatively and by way of further non-limiting example, they may be fashioned from coils (not illustrated) of more resilient materials such as metals. In place of tabs, illustrated restraining wraps 18, 20, 22 have free ends that facilitate their being grasped, e.g., for positioning of the tips 12, 14, 16 and for removal of the wrapped or coiled restraining members therefrom.

Figure 4:
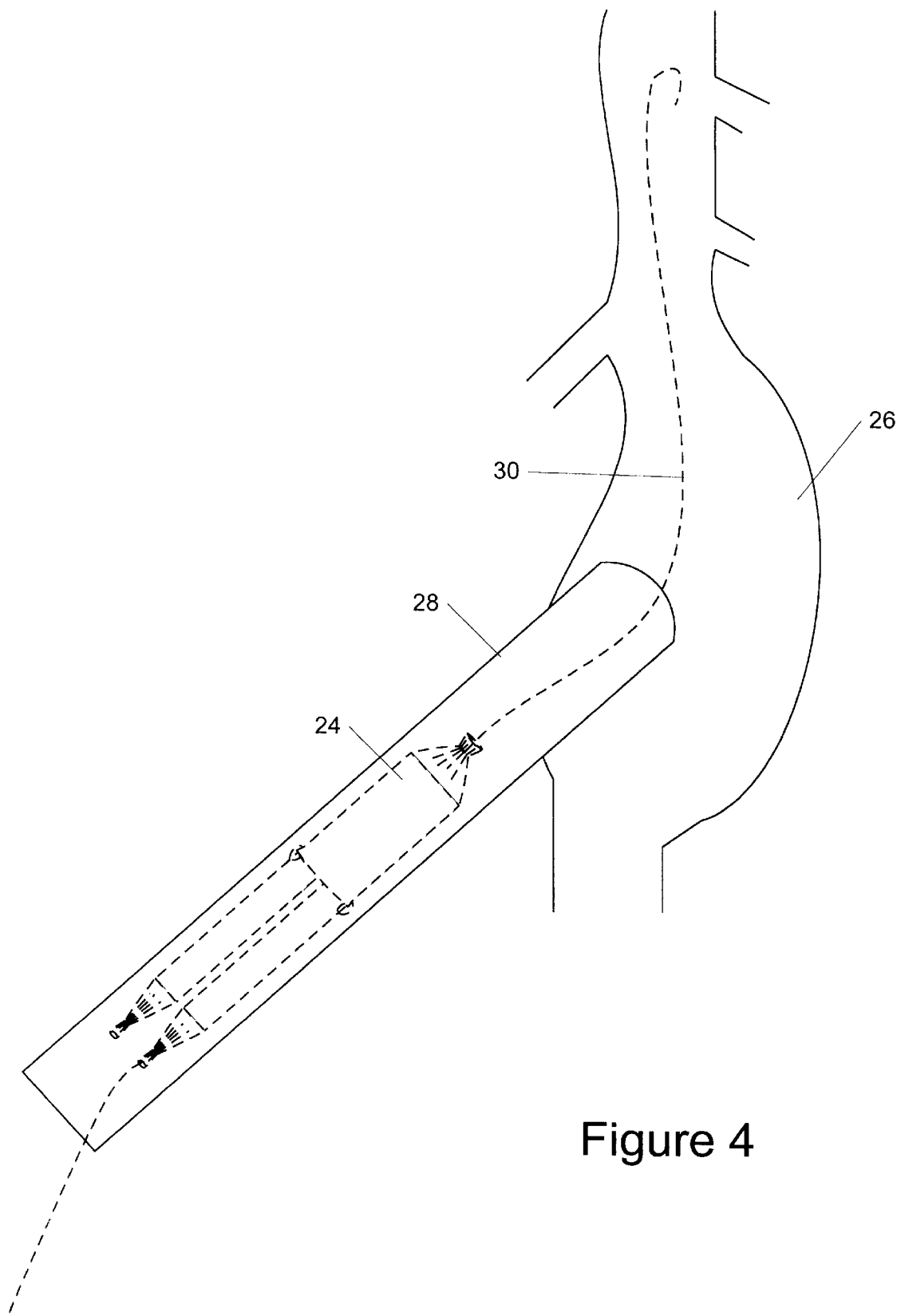
FIG. 4 depicts vascular repair according to the invention.

FIG. 4 depicts a method of vascular repair according to the invention. Here, an encapsulated stent-graft 24 is passed percutaneously, directly through an aortic aneurysm 26, without the need for surgical exposure of the femoral arteries. Deployment proceeds as described below.

Using a low translumbar approach, percutaneous access to the aorta is gained. A double- ended stiff guidewire 30 is placed through this access into the thoracic aorta. After dilating the tract to 30 French or larger, a 30 French or larger introducer sheath 28 is placed into the aneurysm 26. Over the guidewire 30, the encapsulated stent-graft 24 is pushed into the aorta using a pusher (not shown).

A catheter loop-snare (not shown) is placed through a vascular sheath in an axillary artery is used to snare the guidewire 30 and pull it from the introducer sheath 28 completely into the aorta. Using catheter loop-snares through common femoral artery vascular sheaths, the capsules 20, 22 covering each iliac tip 14, 16 of the stent-graft 10 are grasped in order negotiate each tip 14, 16 into a respective iliac artery. Using the catheter loop-snare placed from above, the capsule 18 covering the aortic tip 13 of the stent-graft 10 is grasped to position that tip for deployment immediately below the renal arteries. Snaring of the capsules 18, 20, 22 permits safe manipulation of the stent-graft 10 without risk of premature deployment.

When properly positioned, the snares are repositioned onto tabs at the ends 18a, 20a, 22a of the capsules 18, 20, 22. The "break-away" sutures 20b, 20c are then broken with gentle traction and the aortic capsule 18 is retracted via pulling it in a central-to-peripheral direction (i.e., pulling it off the end of the limb 12), deploying the aortic limb 12 of the stent-graft. Subsequently, with fluoroscopic guidance to ensure lack of migration of the aortic limb 12, the iliac limb capsules 20, 22 are retracted, again, via pulling them in central-to-peripheral directions, deploying the iliac limbs 14, 16 of the stent-graft. The carrier capsules 20, 22 are removed through sheaths in the femoral arteries and the axillary artery. The guidewire 30 remains in the lumen of the stent-graft 10 to permit other interventions such as balloon angioplasty if necessary. If no leak into the aneurysm is present, the 30 French 28 sheath can be removed without A consequence, as its entry site is excluded from the circulation by the stent-graft.

In an alternate practice, the aortic limb 12 is deployed from the flank introducer sheath, then the iliac limbs 14, 16 are pushed out of the introducer 28 into the aneurysm 26 sac, where they are snared from below and Wallstented.

The above-described constructions and techniques may be utilized in the repair (or reinforcement) of other vascular cavities, as well. In addition, those constructions and techniques may be applied using stent-grafts other then the illustrated bifurcated aortic stent-graft 10. For example, a tubular stent graft system, comprising two tips (one cephalad and one caudal) and two respective capsules, may also be utilized for vascular repair.

Described above are systems, devices and methods meeting the desired objects. Those skilled in the art will appreciate that the embodiments illustrated and described herein are merely examples of the invention and that others systems, devices and methods incorporating changes therein also fall within the scope of the invention, of which I claim:

1. A method of vascular treatment comprising:
   A. inserting into a vascular cavity a stent-graft system comprising
      i. an expandable tip,
      ii. a restraining member disposed about at least a portion of the tip, the restraining member constraining expansion of the tip,
   B. positioning at least the tip and restraining member at a desired location in the cavity, and
   C. removing the restraining member from the tip of the stent-graft via a motion in a central-to-peripheral direction.

2. A method according to claim 1, wherein the restraining member constrains expansion of the tip even absent contact with means by which the stent-graft is deployed.

3. A method according to claim 1, wherein step (C) comprises slidably removing the restraining member from the tip.

4. A method according to claim 1, wherein the restraining member is detachably affixed to the tip.

5. A method according to claim 4, wherein the restraining member is detachably affixed by any a suture, hook, aperture, button, hook-and-loop, and friction seal to the tip.

6. A method according to claim 1, wherein step (B) comprises grasping the restraining member in order to position the tip in the cavity.

7. A method according to claim 1, wherein step (C) comprises detaching the restraining member from the stent-graft in order to remove it from the tip.

8. A method according to claim 7, wherein step (C) comprises any of breaking a suture and detaching a hook in order to remove the restraining member from the tip.

9. A method of treatment of an abdominal aortic aneurysm, comprising of
- A. inserting a stent-graft into one or more of a patient's aortic artery and iliac artery in a vicinity of the aneurysm, the stent-graft comprising:
  - i. an expandable tip,
  - ii. a restraining member disposed about at least a portion of the tip, the restraining member constraining expansion of the tip,
- B. positioning at least the tip of the stent-graft and restraining member at a desired location in one or more of the aortic and iliac arteries, and
- C. removing the restraining member by sliding it from the tip of the stent-graft in a central-to-peripheral direction.

10. A method according to claim 9, wherein the restraining member constrains expansion of the tip even absent contact with means by which the stent-graft is deployed.

11. A method according to claim 9, wherein step (C) comprises slidably removing the restraining member from the tip.

12. A method according to claim 9, wherein step (A) comprises inserting the stent-graft directly into an abdominal aortic aneurysm.

13. A method according to claim 9, wherein step (A) comprises pushing the stent-graft into the aneurysm via a translumbar, percutaneous approach.

14. A method according to claim 13, wherein step (B) comprises grasping the restraining member with a catheter loop-snare in order to position a tip of the stent-graft into one or more of the aortic and iliac arteries.

15. A method according to claim 14, wherein step (C) comprises detaching the restraining member from the stent-graft by grasping it with a catheter loop-snare.

* * * * *